United States Patent [19]
Killam

[11] Patent Number: 5,275,167
[45] Date of Patent: Jan. 4, 1994

[54] ACOUSTIC TRANSDUCER WITH TAB CONNECTOR

[75] Inventor: Donald G. Killam, Woodinville, Wash.

[73] Assignee: Advanced Technology Laboratories, Inc., Bothell, Wash.

[21] Appl. No.: 929,736

[22] Filed: Aug. 13, 1992

[51] Int. Cl.$^5$ ............................................. A61B 8/00
[52] U.S. Cl. ................................ 128/662.03; 310/334; 29/25.35
[58] Field of Search .................. 128/662.03, 661.01; 310/334; 29/25.35

[56] References Cited

U.S. PATENT DOCUMENTS

| | | | |
|---|---|---|---|
| 4,217,684 | 8/1980 | Brisken et al. | 29/25.35 |
| 4,326,418 | 4/1982 | Pell, Jr. | 73/644 |
| 4,348,904 | 9/1982 | Bautista, Jr. | 73/644 |
| 4,404,489 | 9/1983 | Larson, III et al. | 310/334 |
| 4,411,052 | 10/1983 | Kampf | 29/25.35 |
| 4,545,041 | 10/1985 | Tims et al. | 367/157 |
| 4,551,912 | 11/1985 | Marks et al. | 437/19 |
| 4,591,087 | 5/1986 | Frasch | 228/110 |
| 4,649,415 | 3/1987 | Hebert | 357/74 |
| 4,701,659 | 10/1987 | Fujii et al. | 310/334 |
| 4,776,509 | 10/1988 | Pitts et al. | 228/179 |
| 5,000,663 | 3/1991 | Gorton | 417/63 |
| 5,064,412 | 11/1991 | Henke et al. | 604/65 |
| 5,126,616 | 6/1992 | Gorton et al. | 310/334 |
| 5,180,093 | 1/1993 | Stansbury et al. | 228/1.1 |

Primary Examiner—Francis Jaworski
Attorney, Agent, or Firm—W. Brinton Yorks, Jr.

[57] ABSTRACT

An acoustic transducer assembly is provided in which the signal and reference potential contacts of the elements of the transducer are electrically connected to external circuitry by means of tape automated bonding conductors. At least a first array of TAB conductors is provided for the signal leads to the transducer elements and a second array is provided for the reference potential leads. In a preferred embodiment a uniform reference potential is maintained across the reference potential contacts of the transducer by utilizing TAB conductors connected to each end of the reference potential contacts and leading to a source of reference potential.

9 Claims, 3 Drawing Sheets

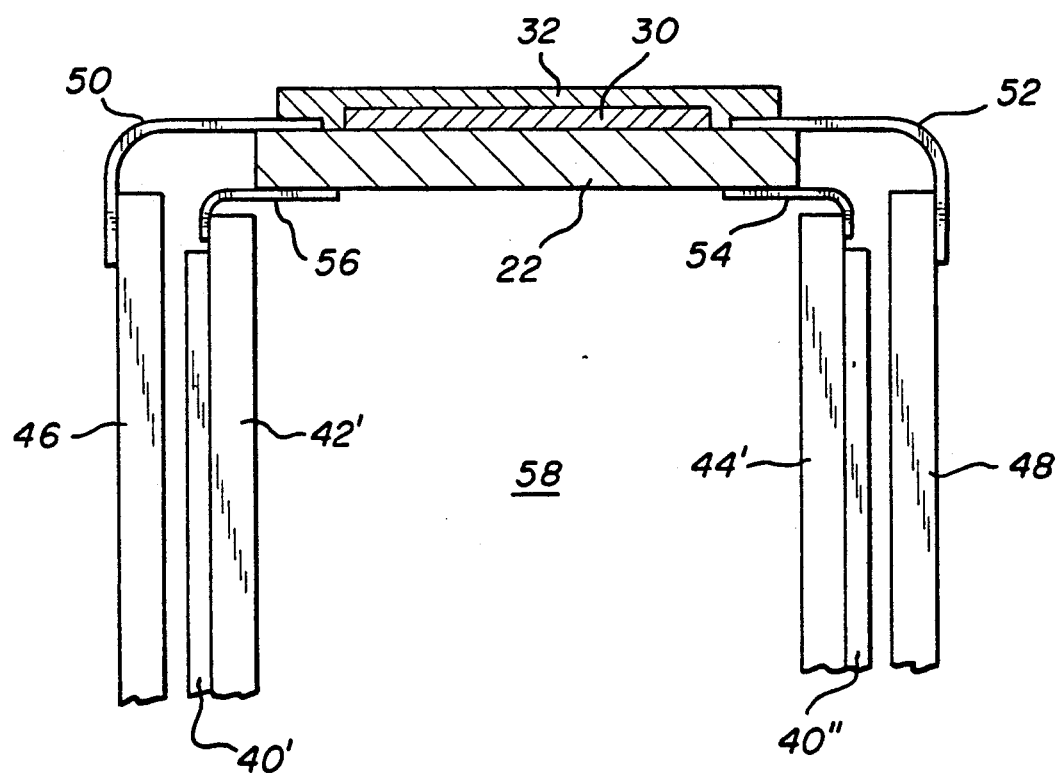

ACOUSTIC TRANSDUCER WITH TAB CONNECTOR

This invention relates to ultrasonic diagnostic systems which utilize ultrasonic transducers to provide diagnostic information concerning the interior of the body and, in particular, to such transducers which utilize tape automated bonding (TAB) connectors to make electrical connections to the acoustic transducer.

Ultrasonic diagnostic imaging systems are in widespread use for performing ultrasonic imaging and measurements through the use of scanheads which are placed against the skin. Such systems are in common use by radiologists, cardiologists, and obstetricians for examinations of the heart, a developing fetus, or internal abdominal organs. These systems operate by actuating an acoustic transducer within the scanhead to transmit ultrasonic energy through the skin and into the body and receiving ultrasonic echoes returned from the internal structure of the body. The transducer converts the acoustic energy of the returning ultrasonic echoes into electrical signals which are coupled by a cable to the diagnostic system for processing and display.

The acoustic transducer is a piezoelectric element which is generally made of a crystalline material such as barium titanate. The piezoelectric crystal may be a single element or may be cut, or diced, into an array of fine elements. Array scanheads are operable in ultrasonic scanning modes known as linear array and phased array operation, in which groups of elements are actuated and used for reception in various combinations. The individual elements of an array transducer are generally rectangular in shape. The elements of high frequency transducers used at frequencies in excess of 7 MHz can be very small with widths ranging down to only a few thousandths of an inch. In addition, the number of these finely dimensioned elements can be considerable, with numbers ranging from 128 elements to in excess of 380 elements. With the numbers of such piezoelectric elements being so great and their dimensions so small, means must be provided for accurately and reliably making the necessary electrical connections between the individual transducer elements and the scanhead cable.

High frequency ultrasonic transducer arrays are intended to receive echoes of the lowest intensity possible at very high frequencies. To meet this objective it is imperative that reliable electrical connections be made to the transducer elements and that the electrical characteristics of the elements be refined to as great a degree as possible. It is essential that no spurious or deleterious electrical conditions be introduced or engendered such as ground current conditions. These conditions could arise if sections of a conductor which are to be maintained at ground or reference potential are not positively and uniformly maintained at that potential. If ground connections are ineffectively made, ground currents could interfere with the reception and electrical translation of the desired acoustic signals.

In accordance with the principles of the present invention an ultrasonic scanhead is provided which includes a transducer comprising an array of adjacent longitudinal elements. The transducer elements are plated on the forward facing surfaces which opposes the subject during use and on the opposite rearward facing surfaces. Electrical connections are made to the element surfaces by groups of unitarily fabricated TAB leads having dimensions and spacings which align with the elements to which the connections are to be made. Ground connections are made by bonding TAB leads to the forward facing plated surfaces and signal connections are made by bonding TAB leads to the rearward facing surfaces. The remaining ends of the TAB leads are bonded to the scanhead cable, preferably by way of conductors on an intermediate printed circuit board.

In accordance with a further aspect of the present invention a layer of impedance matching material overlies the central portion of the forward facing plated element surfaces. To insure the maintenance of a balanced, uniform reference potential on the forward facing plated element surfaces two groups of reference potential TAB leads are respectively bonded to the opposite ends of the forward facing plated element surfaces on either side of the intervening matching layer. The remaining ends of these TAB leads are bonded to an effective reference potential member such as a ground plane or the copper foil of a printed circuit board. This balanced grounding minimizes the induction of ground currents in the forward facing plated element surfaces.

In the drawings:

FIG. 3 illustrates a partial cross-sectional and partial side view of a second acoustic transducer assembly with TAB connections in accordance with the principles of the present invention.

Figure 1A:
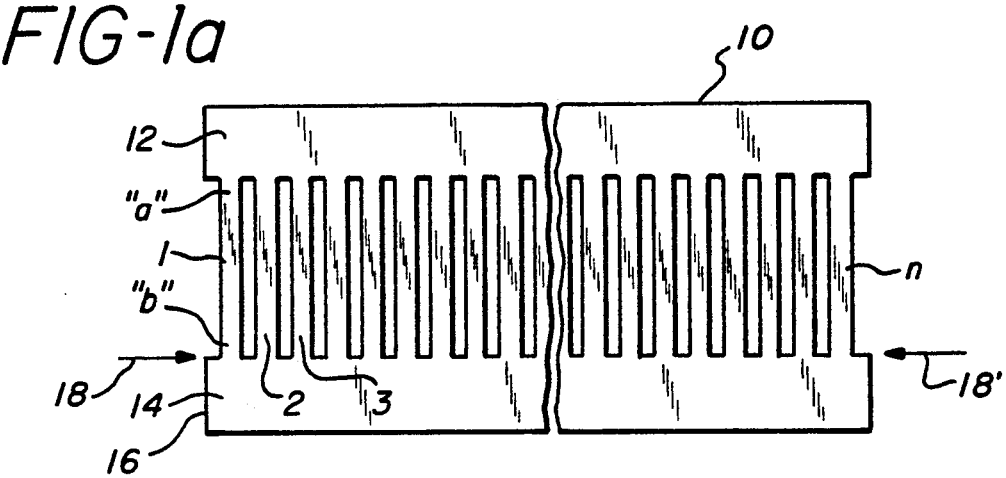
FIG. 1a illustrates an array of TAB leads in alignment with metallized pads on the PZT substrate of FIG. 1b and connected to the substrate pads in FIG. 1c.

Referring first to FIGURE 1a, a joined array 10 of TAB leads is shown. FIG. 1 illustrates an array of "n" leads which are partially numbered from left to right as 1, 2, 3, ... n. Each of the n leads has an upper end "a" and a lower end "b" which is joined to an upper carrier 12 and a lower carrier 14. The leads and the carriers are part of a single, continuous piece of metal or foil which is suitable for use as an electrical conductor such as gold or copper. The array 10 may be formed by any of a number of known techniques such as photolithography and chemical milling or photolithography with metal deposition, which enables the formation of precisely aligned minute conductors. The carriers 12 and 14 maintain the alignment of the conductors during handling prior to use and the flat, planar configuration of the array retards any tendency of the conductors to turn or twist individually.

Figure 1B:
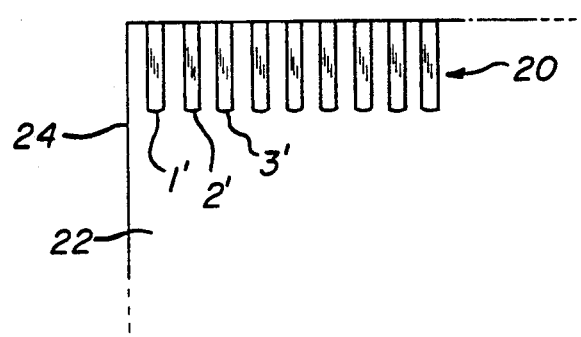

FIG. 1b illustrates a corner of a ceramic PZT substrate such as that which is suitable for use as a piezoelectric acoustic transducer. A group 20 of parallel metallized leads individually identified as 1', 2', 3', ... have been formed on the ceramic substrate by any one of a number of techniques known in the art. These metallized leads 20 are similarly made of metals with good bonding and conductive properties such as gold or copper. Respective ones of the metallized leads 20 are seen to be in alignment with respective ones of the TAB conductors of FIGURE 1a. Since both the TAB leads and the metallized substrate leads may be formed by photographic techniques it is possible to precisely form both groups of leads with matching widths and spacings.

Figure 1C:
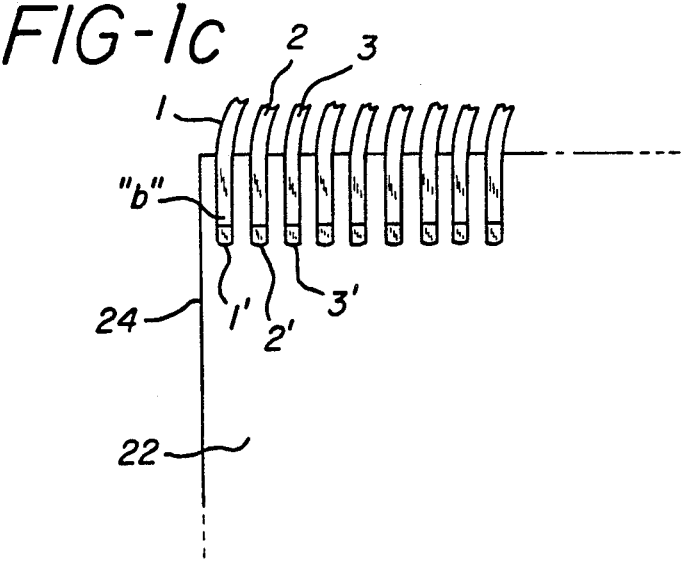

In FIG. 1c the lower ends b of the TAB leads of FIG. 1a have been bonded to the metallized pads on the ceramic PZT substrate. This bonding is precisely accomplished in the illustrated embodiment by aligning the edge 16 of the lower carrier 14 with the edge 24 of the ceramic substrate. Such alignment will correspondingly create an overlapping alignment of individual ones of the TAB leads and the metallized pads. The TAB leads are then bonded to the pads by known techniques such as contact or laser soldering, pulse reflow bonding, or constant temperature soldering. After the TAB leads have been bonded in place the lower carrier 14 is cut away and removed by cutting between the arrows marked 18—18' as shown in FIG. 1a. The lower carrier is discarded, leaving the individual TAB leads bonded to their respective metallized pads on the PZT substrate. The TAB conductors then function to form separate conductive paths between individual transducer elements and corresponding electrical circuitry or printed circuit boards.

In the prior art electrical connections have been made to acoustic transducer elements through metallized patterns formed on flexible polymeric backing sheets such as that shown in U.S. Pat. No. 4,404,489. The present invention provides several improvements over this prior art technique. The polymeric backing of the prior art materials can interfere with soldering, and can melt or distort when exposed to temperatures at which soldering or bonding is performed. The TAB arrays of the present invention have no backing and hence no materials which can be the subject of such problems. Additionally, when connections are made to the prior art materials a line of flexure is formed where leads leave the edge of the backing sheet or intersect the surface. Bending or vibration from shipping or handling can stress the leads at these lines of flexure, weakening the leads or altering their conductive properties. The TAB arrays of the present invention have no such natural lines of flexure and hence are immune to this problem also.

Figure 2:
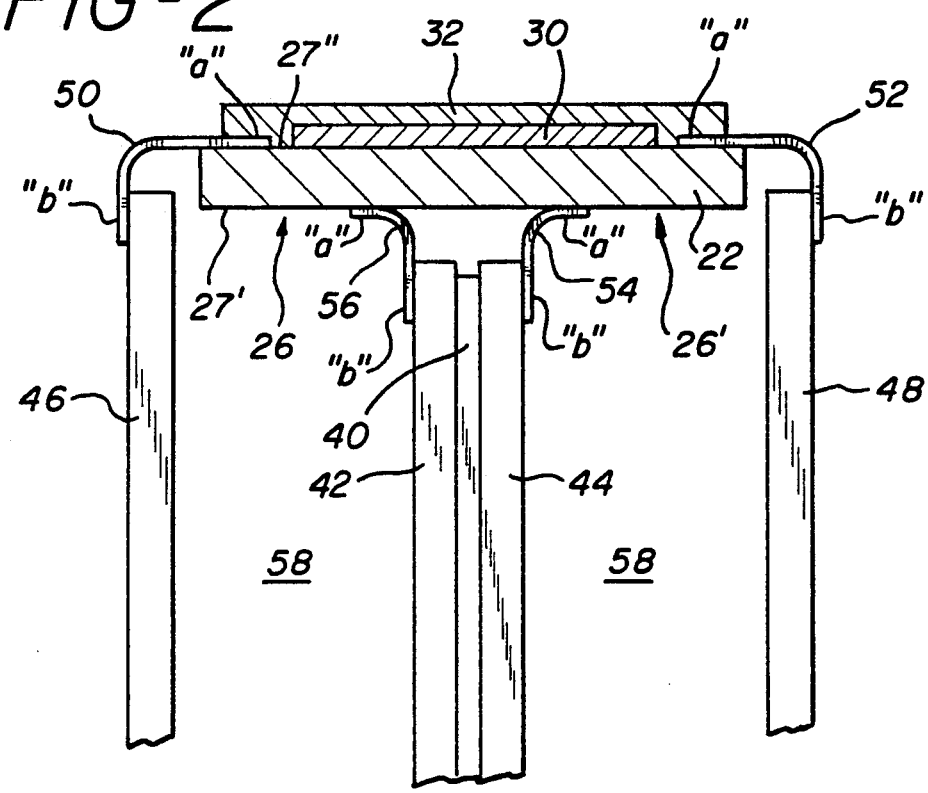
FIG. 2 illustrates a partial cross-sectional and partial side view of an acoustic transducer assembly with TAB connections in accordance with the principles of the present invention.

FIG. 2 illustrates an acoustic transducer assembly with TAB connections constructed in accordance with the principles of the present invention. A rectangular piezoelectric crystal bar 22 is gold plated on its upper surface 27' and on its lower surface 27'. An acoustic impedance matching layer 30 is formed over the central area of the upper surface 27", leaving the edges of the upper surface exposed along the longitudinal dimension of the crystal bar. Two TAB arrays 50 and 52, shown in edge view in FIG. 2, are bonded to the exposed, plated upper surface of the crystal bar in accordance with the technique described in conjunction with FIGS. 1a–1c. A second matching layer 32 is formed over substantially the entire upper surface 27", including the first matching layer 30 and the ends of the TAB leads 50 and 52.

Figure 2A:
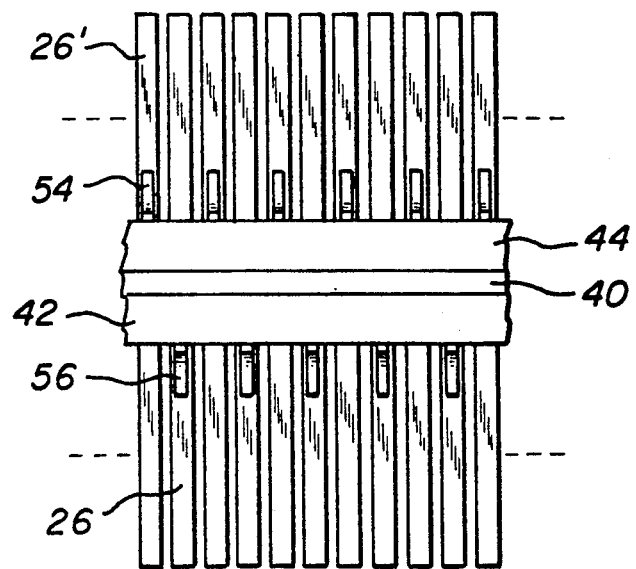
FIG. 2a illustrates the staggered TAB connections to the transducer elements of FIG. 2.

The crystal bar 22 is cut into individual transducer elements by cutting across the bar so that the longitudinal dimension of each element is in the plane of the drawing of FIG. 2. Cutting is done from the lower surface 27' of the crystal bar, through both the upper and lower plated surfaces, and partially into the matching layers. With the crystal bar now cut into individual transducer elements, signal connections are made to each active element. Two printed circuit boards 42 and 44 are joined in a back to back fashion to a copper heatsink 40. Two TAB conductor arrays shown as 54 and 56 are bonded to metallized pads on the two printed circuit boards in the manner shown in FIG. 1c. The carriers on the arrays are cut away to leave the "b" ends of each conductor bonded to a respective metallized pad on the two boards 42 and 44. The "a" ends of the TAB signal conductors are then bonded to respective ones of the plated transducer elements and the remaining carriers of the array are removed. For improved electrical and mechanical isolation between adjacent conductors the TAB leads from each board are connected to alternate transducer elements, and the two printed circuit boards thus make staggered connections to the transducer elements. This is illustrated by the partial view of FIG. 2a of the lower surface 27, of the crystal bar. This view shows for instance that a TAB conductor 54 connects transducer element 26, to printed circuit board 44. The adjacent transducer element 26 is connected by TAB conductor 56 to printed circuit board 42.

A backing box is formed by outer pieces 46 and 48, which can be formed by copper panels or plastic or fiberglas boards with laminated copper foil surfaces. The "b" ends of the TAB conductors 50 and 52 are bonded to the ground shield formed by the copper panels or foil surfaces, thereby making a ground, or return connection to the upper plated surfaces 27" of the transducer elements. The space 58 between the pieces 46 and 48 is filled with acoustic backing material to finish the transducer assembly.

It will be noted that the illustrated assembly utilizes an individual return conductor attached to each end of each transducer element. The use of a return conductor on each end of the elements provides balanced grounding of great integrity, minimizing the occurrence of unequal potentials across the plated surface of the transducer element which can occur if the element is connected to return potential only at one end. This improves the electrical performance of the transducer. The use of two return conductors also provides an additional measure of patient safety in the event that one ground conductor breaks or becomes disconnected from the transducer element or the ground plane. Furthermore, the use of individual TAB leads rather than a continuous sheet of foil or other continuous metal conductor means that it is not necessary to cut through the conductors when the crystal bar is diced into individual elements. This prevents the occurrence of burrs on the edges of conductors, uneven conductor widths, or damage to conductors which can occur when cutting a continuous sheet into individual conductors. In the present invention the crystal bar is diced by cutting between the return TAB conductors.

FIG. 3 illustrates an alternate embodiment of a transducer assembly constructed in accordance with the principles of the present invention. In this embodiment the crystal bar 22, the matching layers 30 and 32, and the return TAB leads 50 and 52 with connections to the backing box pieces 46, 48 are arranged as described in the first embodiment. The signal TAB leads are now connected to separated printed circuit boards 42' and 44', each of which is backed by its own copper heatsink 40', 40". The printed circuit boards are disposed on either side of the transducer elements and the TAB connections 54, 56 to the individual transducer elements are made to the ends of the elements in alternate, staggered fashion. This arrangement leaves an unobstructed space 58 behind the transducer elements which is filled with acoustic backing material, and affords ease of repair because the TAB connections extend outside the backing material filled area. The arrangement of FIG. 3 could be further consolidated if desired by utilizing the copper heatsinks 40', 40" for connection of the return TAB leads in place of the separate pieces 46, 48. Utilizing the copper heatsinks for ground return will eliminate pieces 46, 48 from the design.

What is claimed is:

1. An ultrasonic transducer assembly comprising:
    a plurality of piezoelectric transducer elements;
    transmission and reception means for transmitting signals to or receiving signals from said elements; and
    means for connecting individual ones of said transducer elements to respective points of said transmission and reception means, said connecting means comprising a plurality of unitarily fabricated tape automated bonding conductors.

2. The ultrasonic transducer assembly of claim 1, wherein said connecting means further comprises a carrier unitarily fabricated with said conductors and attached to the ends of a plurality of said conductors, wherein said carrier maintains the alignment of said ends of said conductors and said carrier is removed when said conductors are affixed in place.

3. The ultrasonic transducer assembly of claim 2, wherein said connecting means further comprises a second carrier unitarily fabricated with said conductors and attached to the other ends of said plurality of conductors.

4. The ultrasonic transducer assembly of claim 1, wherein said connecting means comprises a first array of tape automated bonding conductors connected to signal potential points of said transducer elements and a second array of tape automated bonding conductors connected to reference potential points of said transducer elements.

5. The ultrasonic transducer assembly of claim 4, wherein the conductors of said first array are connected to alternate ones of said transducer elements, and further comprising a third array of tape automated bonding conductors respectively connected to the remaining alternate ones of said transducer elements.

6. The ultrasonic transducer assembly of claim 2, wherein said connecting means further comprises third and fourth carriers unitarily fabricated with respective ones of said plurality of conductors and attached to the other ends of each of said plurality of conductors.

7. An ultrasonic transducer assembly comprising:
    a plurality of longitudinal piezoelectric transducer elements, each having a signal potential surface and a reference potential surface;
    transmission and reception means for transmitting signals to or receiving signals from said elements; and
    means for connecting individual ones of said transducer elements to said transmission and reception means, said connecting means comprising a first plurality of unitarily fabricated tape automated bonding conductors respectively connected to first ends of said reference potential surfaces and a second plurality of unitarily fabricated tape automated bonding conductors respectively connected to second ends of said reference potential surfaces.

8. The ultrasonic transducer assembly of Claim 7, wherein said connecting means further comprises first and second carriers unitarily fabricated with each of said plurality of conductors and respectively attached to the ends of said plurality of conductors, wherein said carriers maintain the alignment of said ends of each of said plurality of conductors and said carriers are removed when said conductors are affixed in place.

9. The ultrasonic transducer assembly of claim 6, wherein said connecting means comprises a first array of tape automated bonding conductors connected to signal potential points of said transducer elements and second and third arrays of tape automated bonding conductors connected to reference potential points of said transducer elements.

* * * * *